United States Patent [19]

Merkl

[11] 4,093,707

[45] June 6, 1978

[54] PROCESS FOR PREPARING PEROXIDE GROUP CONTAINING ALUMINUM COMPLEX

[76] Inventor: George G. Merkl, 46 Sunset Ct., Haworth, N.J. 07641

[21] Appl. No.: 632,727

[22] Filed: Nov. 17, 1975

Related U.S. Application Data

[63] Continuation-in-part of Ser. No. 176,907, Sep. 1, 1971, abandoned, which is a continuation-in-part of Ser. No. 859,703, Sep. 22, 1969, abandoned, which is a continuation-in-part of Ser. No. 712,888, Feb. 19, 1968, abandoned.

[51] Int. Cl.$^2$ ............................................. C01F 7/02
[52] U.S. Cl. ................................... 423/626; 423/625; 423/244; 423/239; 423/628; 424/68; 424/154; 252/463
[58] Field of Search ............................... 423/625–629

[56] References Cited

U.S. PATENT DOCUMENTS

| | | | |
|---|---|---|---|
| 2,274,634 | /1942 | Heard | 423/627 |
| 2,888,323 | 5/1959 | Teichner | 423/627 |
| 3,039,849 | 6/1962 | Willcox | 423/627 |
| 3,055,736 | 9/1962 | Becue | 423/627 |
| 3,056,725 | 10/1962 | Rinse et al. | 423/629 |
| 3,268,295 | 8/1966 | Armbrust | 423/627 |
| 4,032,623 | 6/1977 | Meckl | 423/625 |

OTHER PUBLICATIONS

Tanake, "American Perfumes & Cosmetics", vol. 77, 1962, pp. 25–30.

*Primary Examiner*—Herbert T. Carter
*Attorney, Agent, or Firm*—Arnold, White & Durkee

[57] ABSTRACT

A peroxide group containing complex of aluminum, oxygen and hydrogen is obtained having an aluminum-/oxygen atomic ratio of about 1:3.

The complex is prepared by reacting, at a temperature below 150° F, aluminum metal of a purity of at least 99.98% by weight with a source of hydrogen ions, such as an aqueous inorganic halogen acid, in the presence of mercury and an oxygen gas-containing atmosphere, the aluminum being partially immersed in the mercury and the source of hydrogen ions, comprising a thin film over the mercury. The thickness of this film is insufficient to cover the aluminum not immersed in the mercury, whereby a portion of the aluminum is exposed to the oxygen gas-containing atmosphere. The complex grows from the exposed surface of the aluminum in the form of an easily frangible self-supporting sheet.

12 Claims, 10 Drawing Figures

PROCESS FOR PREPARING PEROXIDE GROUP CONTAINING ALUMINUM COMPLEX

RELATED APPLICATIONS

This application is a continuation-in-part of U.S. application Ser. No. 176,907, filed Sept. 1, 1971, and now abandoned; which application in turn is a continuation-in-part of U.S. application Ser. No. 859,703, filed Sept. 22, 1969, and now abandoned; which application in turn is a continuation-in-part of U.S. application Ser. No. 712,888, filed Feb. 19, 1968, and now abandoned.

BACKGROUND OF THE INVENTION

This invention relates to a certain peroxide group containing complexes of aluminum, oxygen and hydrogen wherein the aluminum/oxygen atomic ratio is about 1:3, and to methods of producing such complexes.

The common oxide of aluminum is alumina, $Al_2O_3$, which is known to exist in several physical forms and in several states of hydration. Ignoring associated water molecules, the ratio of numbers of oxygen atoms to aluminum atoms is 3 to 2, which in terms of atomic weight ratios is $3 \times 16$ to $2 \times 27$, or in weight percentage terms, 47% to 52% oxygen.

Several forms of alumina are well known. For example, fibrous or hydrated alumina, $Al(OH)_3$ (which is also known as alumina trihydrate, aluminum hydroxide, aluminum hydrate, hydrated alumina, and hydrated aluminum oxide) is discussed in U.S. Pat. No. 2,915,475, and discussed in an article entitled *The Fine Structure and Properties of Fibrous Alumina* by Watson et al, Kollod Zergschuft Band 154 Heft 1 (1957). Fibrous alumina as described in the aforementioned patent and article is a thin, very porous, fibrous, hydrated aluminum structure which is formed on the surface of the aluminum. The structure is pure white in color and exhibits distinct fibrils which are easily seen with the naked eye are 0.1–0.6 microns in width. The structure also contains hydroxyl groups.

Fibrous alumina is typically prepared by dissolving bauxite in a strong caustic solution and precipitating the fibrous alumina from the sodium aluminate solution by neutralization with $CO_2$. Another method is to wash aluminum foil with fresh acetone, sodium hydroxide and water and then amalgamating the foil slightly in a very dilute mercury chloride solution.

A clathrate comprises an expanded atomic lattice of one element or compound in which another element or compound can be trapped. There are complex forces of attraction which retain the trapped substance in the lattice. However, in the case of trapped gases, an increase in temperature generally generates conditions which favor the escape of the trapped gases.

While organic clathrates are relatively common, inorganic clathrates are rare and have previously been regarded as chemical curiosities. Known inorganic clathrates have been formed only by the use of elevated temperatures and extremely high pressures. There are no known methods for the commercial production of inorganic clathrates which have commercial value.

SUMMARY OF THE INVENTION

The present invention provides a peroxy group containing complex of aluminum, oxygen and hydrogen which is distinguishable, in characteristics and properties, from the above-described forms of alumina, and a method of forming such complex.

More specifically, the present invention provides a method for preparing an aluminum-oxygen hydrogen complex containing an excess of oxygen over the normal ratio of 3 atoms of oxygen to 2 atoms of aluminum found in the common aluminum oxide, $Al_2O_3$, which method comprises reacting at a temperature below 150° F, aluminum metal of a purity of at least 99.98% by weight in the presence of mercury, a source of hydrogen ions and an oxygen gas-containing atmosphere, the aluminum metal being partially immersed in the mercury and the source of hydrogen ions comprising a thin film over the mercury, whereby the complex forms on the surface of aluminum metal or mercury-permeated aluminum metal exposed to the atmosphere.

It is believed that the complex obtained by the method of this invention may be an inorganic clathrate which traps some oxygen; accordingly, it is difficult to give a definitive chemical formula or to be precise as to what a single molecule of the complex comprises.

The physical appearance of the complex when prepared by the method previously mentioned and further discussed below is an extremely low density, porous, structurally self-sustaining but relatively fragile delicately bluish-white colored solid which may be broken up into a powder and which may contain as much as 75–85% by weight of oxygen. When the complex is heated at atmospheric pressure to a temperature of approximately 150° C or over, gaseous diatomic oxygen is given off. Even at a temperature of 100° C there is an immediate loss of approximately 30% by weight from the complex and oxygen is easily detectable in the vicinity of the compound. When heated to approximately 800° C, there is an additional loss of 25% by weight. After continued heating there is no further evolution of gas and the residue is high purity alumina. This would be consistent with the complex being a higher oxide of aluminum in a clathrate form trapping further oxygen.

Figure 6:
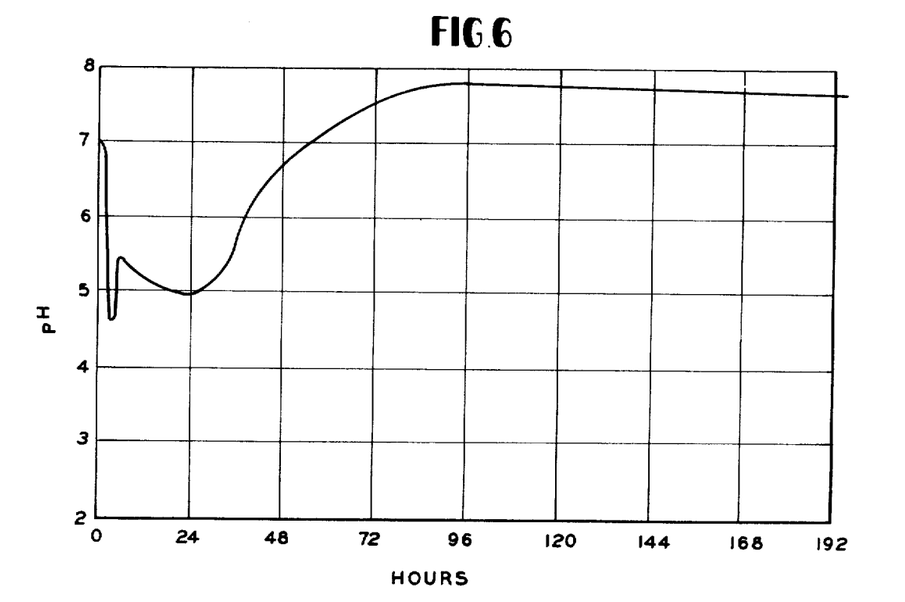
FIG. 6 is a pH curve of the complex of the present invention
Figure 7:
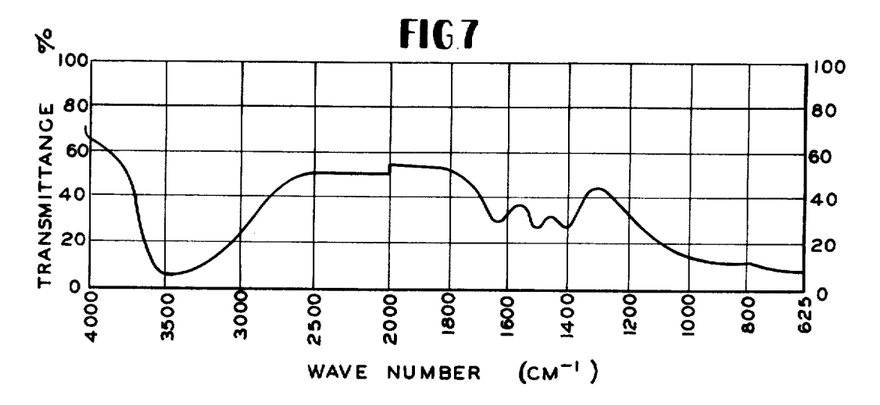
FIG. 7 is an infra-red graph of the complex of the present invention.
Figure 8:
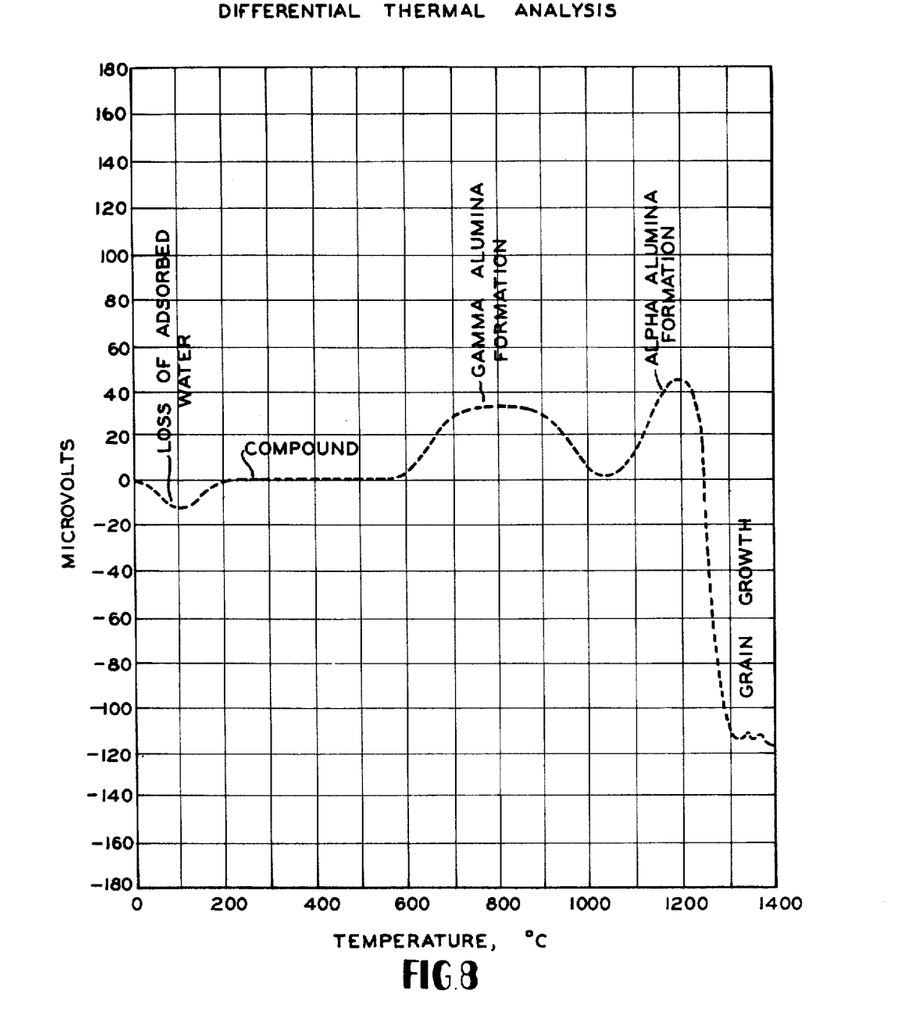
FIG. 8 is a differential thermal analysis curve of the complex of the present invention.
Figure 10:
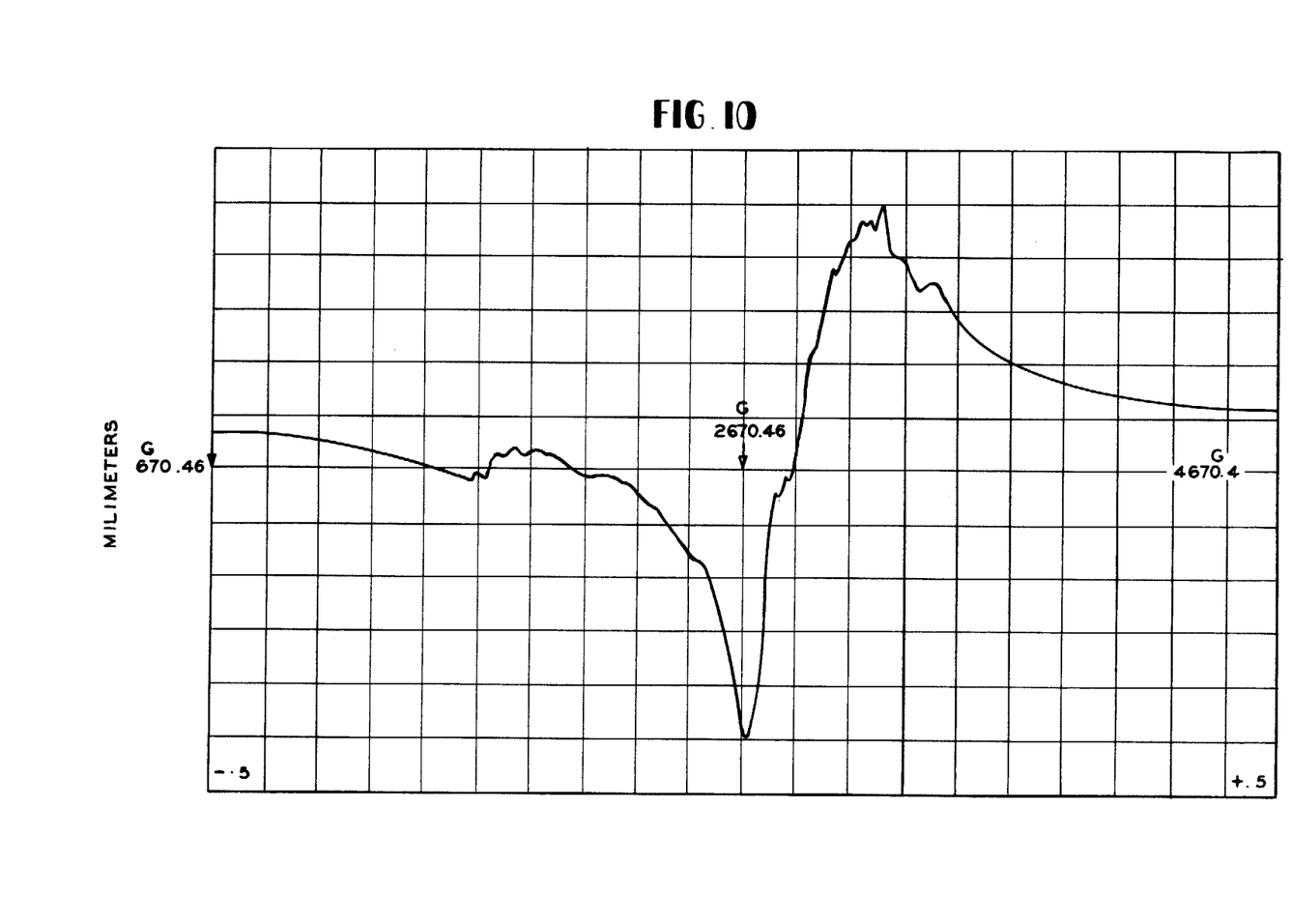
FIG. 10 is an ESR curve for the complex of the present invention.

More specifically, the complex of the present invention is characterized by the presence of peroxide groups and further characterized by the following:

(a) a chain length of 40–200 A; and
(b) a surface area of about 290–500 m²/gram at 350° C;
(c) a pH curve substantially as illustrated in FIG. 6 for a 0.5% aqueous solution;
(d) an infra-red spectra curve substantially as illustrated in FIG. 7;
(e) a differential thermal analysis substantially as illustrated in FIG. 8; and
(f) an energy level diagram substantially as illustrated in FIG. 10.

The complex of the present invention has many uses, including use as a source of gaseous oxygen. However, possibly because of the clathrate structure, the complex can also be used to absorb other gases and liquids and the complex can be used as an agent for occluding or purifying gases, a liquid purifier, a cosmetic carrier, a carrier and supplemental oxygen supplier for combustible compounds, a medicament for burns, a filtering agent, an agent for the formation of gelled gases and many others.

Thus, due to their highly basic character, the complexes of the present invention have the property of absorbing gases, e.g., $SO_2$, $NO_2$, NO, etc. from a gas stream as demonstrated by potentiometric acid titration, and thus, significant utility in connection with the mitigation of air pollution problems as indicated. The complexes described herein, due to the high hydroxyl ion activity and high purity, serve as excellent intermediates for the preparation of aluminum chlorhydrate which is widely used in the preparation of anti-perspirant formulations. The complexes are also effective in inhibiting spore germination with Monolinia Fructicola, Steaphylium Sacrinae Forme and Aspergi-los Niger (Fungi). Significant pest control utility is indicated.

The complexes described herein possess an extremely large surface area, positive surface charge, high purity and active oxygen content. As is well known, a number of reaction systems are catalyzed by materials having a very high surface area. The present aluminum complexes are admirably suited for such purposes; moreover, pelletization of the complexes does not drastically reduce the surface area/weight relationship. Thus, excellent catalytic utility in connection with oxidation, e.g., preparation of dyes, pigments and pharmaceutical intermediates, quinones, aldehydes, peroxides, certain ketones and acids and polymerization reactions is indicated.

The complexes of the present invention also exhibit significant inhibition effects on a variety of microorganisms and, in addition, the effect on the coagulation of bovine serum albumin is of the same order as for freshly prepared aluminum hydroxide. However, the complex of the present invention can be more easily filtered and centrifuged. Apparently, the effect on micro-organisms can be attributed to either an inhibition of the respiratory enzymes or to a coagulating effect on the cellular proteins, with the former being more probable.

A wide variety of other interesting utilities are also indicated for the complexes of the present invention. Thus, the products may be used as lubricating oil additives. With respect to cosmetic applications the unique properties of an extremely large surface area, positive surface charge, high purity and small particle size prove highly beneficial. Investigation indicates the novel complexes to be non-toxic as well as harmless after frequent exposure to the epidermis. Thus, the complexes can be used as a base in the formulation of cosmetic and medicinal creams since it is capable of significantly increasing the viscosity of a number of organic liquids, e.g., as a solid aerosol carrier. The complexes, due to their hydroxyl ion activity which is substantially higher than known alumina and other known aluminum-oxygen compounds, can be used as anti-acid agents since they are not harmful when ingested in moderate amounts. Other utilities of the present complexes include, without necessary limitation, skin cleaning functions due to their effective dehydration activity and absorption capacity for organic compounds (can be used as a powder-on skin cleaner prior to the application of the softening creams); dentifrice compositions based upon their bacteria killing activity and abrasive capacity and small particle size; and purification agent due to their excellent bactericidal action and flocculating capacity.

DESCRIPTION OF PREFERRED EMBODIMENTS

The peroxide group containing complex of aluminum, oxygen and hydrogen of the present invention is believed to be formed in a monomeric form, polymeric form as well as mixtures thereof. The expression "complex" is intended to embrace each of these forms as well as the clathrate structure, including trapped oxygen.

The method of the present invention involves reacting, at a temperature below 150° F, aluminum metal of a purity of at least 99.98% by weight with a source of hydrogen ions, such as an aqueous inorganic halogen acid, in the presence of mercury and an oxygen gas containing atmosphere, the aluminum, typically in the form of a rod, being partially immersed in the mercury. The source of hydrogen ions comprises a thin film over the mercury, with the thickness of this film being insufficient to cover the aluminum. As a result, a portion of the aluminum is exposed to the oxygen gas-containing atmosphere and the complex of the present invention grows from the exposed surface of the aluminum in the form of an easily frangible self-supporting sheet.

The mercury, being essentially a catalytic agent, and not part of the final product, reacts with the source of the hydrogen ions, aluminum electrons and negative ions (such as the halogen in a halogen acid) inside the aluminum to produce ultraviolet radiation. The radiation reorients the aluminum structure by raising its energy level in the presence of hydrogen ions to cause their combination with the aluminum and with oxygen that is present in the area surrounding the aluminum to form the complex of the present invention. The mercury also acts in concert with the aluminum to cause a field effect around the aluminum. This field effect which is generated by means of an electrical potential difference between the aluminum and the mercury, causes the hydrogen ions (protons) and mercury to be pushed or drawn through the aluminum to place the hydrogen ions in a position to form the complex. The field effect also causes some ionization of the surrounding atmosphere to produce active oxygen and some OH$^-$ radicals (the latter being produced from water vapor). The source of hydrogen ions, such as a halogen acid, also produces an electrolytic reaction which acts in concert with the field effect to draw the protons through the aluminum. When the protons reach the surface of the aluminum, they combine with oxygen and aluminum (and some hydroxyl radicals) to form the complex.

The aluminum itself is preferably a high purity aluminum such as 99.99 or 99.98% purity aluminum and should not be heat treated, worked or deformed in any way. If the purity of the aluminum is below 99.99 or 99.98% pure this will not prevent formation of the complex, but will only diminish its purity and stability. There is, of course, a level of purity below which the amount of complex produced will be negligible.

In general, aluminum of at least about 99% purity is suitable. However, it will be recognized that in certain instances departures from the foregoing limitation may be permitted without departing from the true scope of the invention. Accordingly, any designation of purity is merely meant to exclude materials which exhibit a pronounced tendency to diminish the extent of hydrogen ion absorption into the aluminum. The presence of certain metals is beneficial and their use is not excluded by the present invention. However, beyond certain concentration limits, even "beneficial" materials may cause deleterious effects. Accordingly, expressions regarding the purity of the aluminum should be interpreted as excluding materials which significantly diminish hydrogen ion absorption whether the exclusion be on a materials or concentration basis. Thus, it has been found that certain impurities will adversely affect the interaction between mercury and the source of hydrogen ions so as to impair the generation of ultraviolet radiation at the proper energy level. These impurities diminish the extent of hydrogen ion absorption into the aluminum and the generation of ultraviolet radiation depends on this factor. Thus, since these impurities substantially diminish the rate and extent of absorption or diffusion of hydrogen ions into the mass of aluminum, they thereby decrease the yield of the complex of the present invention, since its growth depends on the availability of large quantities of hydrogen ions. The impurities will cause scattering which produces high temperatures and leads to hydrogen ion starvation. Some of these impurities are chrominum, copper, iron, silver, molybdemum, nickel, tungsten, and coblat.

But, certain metal will enhance diffusion of hydrogen ions (protons) into the mass of aluminum. These metals include, without necessary limitation, cesium, vanadium, zirconium, barium, lanthanum, hafnium, titanium, thallium, palladium, and niobium. However, while these metals enhance the diffusion of hydrogen ions, they also may have some deleterious side effects when present in larger amounts, e.g., they scatter the hydrogen ions somewhat inside the aluminum and can cause local reactions leading to exothermic hot spots which can cause the reaction to overheat and thus should only be used in limited quantities, e.g. up to about 0.05% by weight of the aluminum. Above this value, the complex obtained is relatively less stable due to hot spot formation which impairs hydrogen ion diffusion.

Another metal that may be present in the aluminum is magnesium. Magnesium has two effects. Firstly, since it has a higher electromotive activity than aluminum, it reacts with ultraviolet radiation in the atmosphere to generate large amounts of heat; in quantities of less than 1%, the increased activity aids the process by causing the complex to form faster, but in quantities of more than 1% the reaction goes too rapidly and the amount of heat generated then must be taken away by cooling or the reaction will be terminated. Also, in excess quantities, the magnesium tends to cause the production of more unstable products. One of these is an aluminum-magnesium-hydrogen-oxygen compound.

There are other metals which tend to inhibit the diffusion of the hydrogen ions (protons). The metals may be deliberately employed to reduce the rate of reaction so long as the entire reaction is still sustained. Still other metals, one being copper, tend to destroy the reaction entirely. Copper destroys the reaction by preventing the mercury from permeating into the aluminum and also by combining with hydrogen ions before the aluminum can. In quantities of less than 0.2%, the copper permits the reaction to continue but entraps quantities of nitrogen in clathrate form inside the structure of the complex formed.

Thus, expressions with regard to the purity of the aluminum as used herein should be accorded a significance consistent with the limitations explained in the preceding discussion. In any event, desired or optimum concentrations of a particular metal can be readily determined under specific circumstances.

As to the physical form of the aluminum, it must be compatible with the reaction dynamics. Since the aluminum is partially immersed in liquid mercury in accordance with the method of the present invention, it is preferable to choose self-supporting rods or the like. Small pieces of aluminum or powdered aluminum are difficult to use since they tend to become completely engulfed in the mercury, and prevent the hydrogen ions from reaching them. This terminates the reaction. Also, the field effect cannot be produced because the aluminum ultimately becomes completely immersed in the mercury.

However, it will be understood that the aluminum as supplied for use in the process may be in particulate, i.e. subdivided or triturated form, the primary requirement being that such aluminum particles be capable of being suspended, i.e., floated, in the mercury bath such that a portion, preferably in the neighborhood of half its surface area, remains exposed to the atmosphere. In the case of essentially spherical particles, immersion to approximately the midpoint of the particles is preferred. In this manner, the reaction will proceed; however, as the aluminum compound forms, a point will be reached at which the aluminum particle sinks, i.e., becomes completely immersed in the mercury bath. The product-forming reaction will thereupon cease. However, such particles may then be removed by any suitable means and the complex recovered from the surface of the aluminum particle. Such a mode of operation is akin to "batch" processing which may be suitable in some instances. However, the use of larger masses of aluminum, e.g., rods of any configuration, i.e., spherical or polygonal, would be preferable in those instances where a more continuous type of processing is desired. In either case, the complex formed can be simply removed from the parent aluminum mass be such simple mechanical means as scraping or blowing.

For the reaction to take place, the hydrogen ions and mercury must be able to penetrate the aluminum. If the aluminum is covered with surface oxidation, neither the mercury nor the hydrogen ions can get through to the aluminum. Thus, the surface of the aluminum has to be free from oxidation.

This oxidation is generally formed since under ordinary circumstances aluminum exposed to the air rapidly acquires a relatively thin but unbroken surface oxide film of $Al_2O_3$. The oxide may be stripped from the aluminum by any one of a number of well known methods. For example, if a halogen acid is used as the source of protons, in this process, the halogen aicd will also act to strip the oxidation from the aluminum. $Al_2O_3$ does not dissolve in halogen acid, but the halogen acid vapor penetrates the oxide layer to the aluminum beneath to cause the oxide to be broken free of the aluminum (delaminated) to thereby deoxidize the aluminum surface.

The Mercury

Mercury, one of the basic components of the process, acts to permeate through the aluminum crystal lattice. In so doing, it has four basic functions. Firstly, the mercury and the hydrogen ions coact in such a manner so as to cause them both to permeate through the aluminum. Secondly, since the mercury and the aluminum are at different electrical potentials, a field effect about the aluminum is created between the two. The effect causes the permeation of the hydrogen ions through the aluminum crystal lattice and is a basic part of the process. Without this field effect there would be little, if any, permeation of the hydrogen ions through the aluminum. The next function of the mercury is to assist in the generation of ultraviolet radiation in the aluminum itself. The ultraviolet radiation is generated by the energy interaction between the mercury, the aluminum and the source of protons. The final function of the mercury is to act as a coolant in the mass of aluminum. A coolant is needed since the reaction inside the aluminum is sufficiently exothermic, such that a substantial amount of heat is generated. The temperature of the process, however, must not be allowed to exceed 150° F and preferably, should be kept below 120° F for optimum effects. If the aluminum were not cooled, the excessive heat could destroy the entire reaction. It is therefore essential that the mercury or some other medium be present to serve this cooling function.

The mercury itself is elemental mercury; however, mercury compounds which liberate elemental mercury under the conditions of the process or in the presence of ordinary light can be used as long as they quickly and easily yield elemental mercury without any difficulty. Some mercury compounds that can be used are mercury sulfate, mercury chloride and mercuric oxide. With the latter, ordinary light will break it down into mercury and oxygen gas.

Even though the mercury is a significant part of the process, it is really only a quasi-catalyst since it itself is not part of the final molecular structure.

Also, initially, a supply of mercury is needed to permeate the aluminum; however, once this has been accomplished, no new mercury is needed since the amount that is needed to substantially and, preferably, completely permeate the aluminum is all that is needed to keep the process in effect. Thus, once the aluminum has been completely permeated by mercury (this will happen shortly after the process has been started), the source of additional mercury (such as a mercury bath) can be removed and the process will continue as before without the need for any additional mercury. The mercury in the aluminum will circulate through the aluminum with only a negligible loss so that the amount of mercury in the aluminum is sufficient to cause the process to continue. The amount of mercury in the aluminum is preferably about 1-2% by weight of the aluminum.

The Source of Protons

Hydrogen ions, being an essential component of the structure, must be supplied in sufficient quantity to form the complex of the present invention. The source of hydrogen ions can be any compound that is ionizable to produce protons such as the halogen acids, i.e., HCl, HF, HI, and HBr; any water soluble or dispersible organic or inorganic acid such as sorbic acid, acetic acid, and water or alcohol, or any other compound which will readily ionize to yield $H^+$ ions (protons) under the conditions of the process is suitable. If water is used, hot water is preferred over cold water since it is more active. Water is not preferred since it is not sufficiently viscous. The source of protons should be more viscous than water.

Probably the most desirable reagents are the halogen acids, since they are sufficiently viscous and contain negative radicals, e.g., $Cl^-Br^-F^-I^-$. The negative radicals aid in the production of the ultraviolet radiation within the aluminum. The source of protons should also be one that is in an aqueous solution, since then water will also be present to be used as a source of hydroxyl groups.

If a halogen acid is used, it should have a low concentration, otherwise the supply of halogen ions will be so great as to cause a runaway action. A typical reagent will have halogen acid in a concentration of 1N solution. If the reagent is lower in concentration than 1N, the reaction is cooler and a loose or light density product is produced. When the reagent is higher in concentration then 1N, the denser compound is produced.

Hydroxyl radicals ($OH-$) are an important part of the method since they combine to form the peroxide groups ($HO_2$) which are an essential part of the complex of the of the present invention. The hydroxyl radicals are generated from compounds having $OH-$ groups which are readily ionizable under the conditions of the method. Since the method is carried out in the presence of an oxygen-bearing atmosphere, the hydroxyl groups are formed from the reaction of the protons and the oxygen source. In the usual case, some of the hydroxyls are produced in the water.

The hydroxyl radicals can also be produced from the water present in the aqueous solution of the reagent and/or from water vapor present in the atmosphere surrounding the reaction situs. Hydroxyl radicals can also be generated from organic acids, alcohols, etc. or any other readily ionizable source of $OH-$ groups. Still another source of $OH-$ groups is that as the halogen acid removes the oxidation from the aluminum, some of the protons from the acid will combine with the oxygen in the $Al_2O_3$ to form $OH-$ groups.

Oxygen, which is an essential constituent of the complex of the present invention, is generated from the surrounding air atmosphere. Oxygen molecules are quickly absorbed into the complex from the atmosphere. However, it will be appreciated that any other source of $O_2$ would operate equally as well. There also must be sufficient oxygen to form the free oxygen which is presumably held in clathrate form.

Oxygen also will cause the generation of peroxides directly, thus eliminating the need for some of the $OH-$ radicals. The peroxide is generated as follows: The ultraviolet radiation produced by the reaction will cause oxygen in the air to form ozone. The ozone then contacts water present in the reaction to form peroxide.

According to normal chemical reaction dynamics, an increase in temperature will tend to increase the rate of reaction in a chemical process, though the yields may be affected according to whether the reaction is exothermic or endothermic, whether side reactions are favored or not, and whether the product is itself thermally stable.

Observations of the reaction show that it is exothermic. Also, the reaction between aluminum and hydrochloric acid, for example, is also known to be exothermic, but a greater quantity of heat seems to be evolved after the reaction has been initiated and appears to come from within the mass of the aluminum. However, if the reaction is conducted in a pool of mercury and with air as the source of oxygen, there also appears to be an endothermic reaction beneath the surface of the mercury wherein a by-product containing nitrogen is formed.

In practice, an elevated temperature above ambient is desirable for the reaction to proceed at a practical rate. It is found, however, that since the reaction is exothermic, if it is allowed to proceed too rapidly, the exothermic reactions predominate and the temperature rises further.

When the temperature lies in the range of 130° F. (54° C.) to 135° F. (57° C.), substantial and significant quantities of nitrogen in amounts of approximately 15% by weight as no appear in the product.

It is also found that the yield of the required aluminum-oxygen complex becomes negligible at approximately 150° F. (66° C.). Higher temperatures also favor the production of the simple aluminum oxide.

Furthermore, if the temperature were allowed to reach 100° C. not only would the aqueous medium begin to boil but any previously formed complex would begin to decompose.

On the other hand, lower temperatures accelerate the reaction when it is conducted with the aluminum metal coated with mercury but not immersed in a mercury bath.

Thus an effective temperature range for the production of the desired complex lies between ambient temperature and 150° F. but a preferred range is between 68° F. (20° C.) and 120° F. (49° C.) with a particularly preferred temperature being around 100° F. (38° C.).

It will be appreciated from the above discussion that various factors need to be considered when selecting the temperature range. If no nitrogen were present in the atmosphere, one could ignore the production of the byproducts containing nitrogen favored by certain temperatures, though the tendency to from alumina could not be ignored.

When the temperature of the reaction is discussed, it should be appreciated that the reaction is occurring on or near the surface of the aluminum and so it is this area where the temperature needs to be controlled. The local temperature near the reaction area may be different from that of the surrounding environment.

Furthermore, the rate of reaction, and hence, the generation of exothermic heat, can be controlled to some extent by the choice of purity of the aluminum material, along the lines discussed above with certain metals favoring the reaction and others inhibiting it.

The vessel in which the reaction is carried out should be inert from attact by any of the reagents used, specifically mercury and the source of protons. Thus, many metals, including ferrous metals, aluminum, copper, and copper alloys, should be avoided. In addition, many plastics contain impurities which may be leached out and poison the reaction. Therefore, a simple, common and inexpensive glass vessel is preferred, unless a special reaction module is designed for the reaction.

The ratios of the basic ingredients in the complex of the present invention should exist at least in their maximum stoichiometric quantities, although this may vary. A proposed structure is such as to require 12 aluminum atoms for 42 hydrogen atoms and 36 oxygen atoms. Thus, the various sources of these must provide them in at least these quantities to produce the desired complex.

In specific amounts, very small quantities of halogen acid appear to be sufficient for the process. A 3% by weight solution of halogen acid appears to be adequate. In addition, the concentration of halogen acid is not critical to the actual formation of the complex. However, the concentration is important with respect to the yield/time ratio and the density of the complex. As the concentration is increased, the amount of protons available will become greater, and thus, the amount of ultraviolet radiation produced and the field effect produced will both be greater and a more stable densely packed product will be formed. A typical range of concentration is a 0.1 to 2N solution.

It has also been found that the use of a higher concentration of hydrochloric acid, greater than one normal, favors a greater yield to time ratio and produces a considerably more dense complex due to more hydrogen ions. Also, the use of hydrogen gas in the reaction increases the yield to time ratio and enhances the stability of the complex. The use of hydrogen gas will increase the density of the product because more H+ bridges are formed. It is noted that the hydrogen ions absorption and concentration is related to the surface to volume ratio of the aluminum because of the field effect as well as to the external and internal pressure in the aluminum, and the temperature and radiation level.

The density of the gas surrounding the aluminum, that is, the gas to be absorbed, such as the oxygen, should be maintained at as high a value as possible around the surface of the aluminum.

The amount of mercury necessary appears to be an amount that will substantially completely permeate, i.e., saturate the aluminum being used. This can be determined by observing the aluminum sinking into the mercury. When the aluminum is sufficiently permeated with mercury, it will hold about 1-2% by weight. The aluminum rod at this point will become completely coated with mercury and become fragile. For example, if the aluminum is a rod immersed halfway in a bath of mercury, when the rod is sufficiently permeated with mercury the mercury will begin to seep out of the top of the rod so that the rod appears to be completely wetted with mercury. Once the aluminum has been sufficiently permeated with mercury, the source of mercury, such as the mercury bath, can be removed. Mercury is not used up in the reaction and therefore, the amount necessary to completely permeate the aluminum is all that is needed. If a less than sufficient quantity of mercury is present, and the entire inside of the aluminum is not permeated with mercury, then the field effect will only develop to a limited extent. This will result in a limited supply of the complex being produced.

Also, if a mercury-bearing compound such as mercuric oxide is used instead of elemental mercury, then the amount of mercury compound needed is the amount that will produce sufficient elemental mercury for the process. In any event, it is preferable to use elemental mercury.

Mercury is a significant factor in both the production of ultraviolet radiation and also in the production of the field effect outside the aluminum. A sufficient amount of mercury then must be present to produce both of these results. If there is insufficient mercury to produce either of these, then the entire process will not proceed. The amount of mercury necessary to permeate the entire aluminum is approximately the same amount that is necessary to produce the proper electrostatic field outside the aluminum and also the proper internal ultraviolet field inside the aluminum. By enough mercury to completely permeate the aluminum is meant the amount that will fill up all the channels between the grain boundaries of the aluminum matrix. By way of example, and without intending it as a limitation, 100 grams of aluminum are substantially completely converted to the complex of this invention by the use of about 2 grams of mercury.

One simple way of determining when the aluminum has been properly permeated by the mercury is that the aluminum is readily breakable at that point. For example, an aluminum rod can be easily broken by a person of normal strength with a single bend of about 120° when it has been completely permeated by the mercury. At this point, the aluminum has approximately the same hardness as babbit metal.

It should also be pointed out that when a hydrogen ion source other than a halogen acid is used, the anion component of the halogen acid (the Cl− of HCl), will not be available to act in conjunction with the mercury and aluminum to produce the ultraviolet radiation within the aluminum itself. Some other source for producing ultraviolet or other radiation will have to be provided. This can be accomplished by the use of an external U.V. source. The amount of this radiation will have to be sufficient in any case to cause the outer electrons in the aluminum to be raised to a high enough energy level so that the aluminum can effectively combine with the protons to form the complex of the present invention.

Also, of course, the aluminum may be pre-treated mechanically or chemically to remove the surface oxide other than by the presently used halogen or other acids, and thus, a supply of the substance needed to remove the oxide will have to be present. However, at present, the use of both the halogen acid and mercury results in a rather simple and efficient process.

Concerning oxygen, under ordinary circumstances when the reaction is conducted in an air atmosphere there is no problem of oxygen stoichiometry. Oxygen is reacted from the air in quantities determined by the amount necessary for the process. As aforementioned, this would be approximately three oxygen atoms for every aluminum atom. Obviously, when the process is conducted in an open vessel there is a large quantity of oxygen available and no problem of oxygen starvation. However, if the process is carried out in a non-air atmosphere, where there is no large supply of oxygen present, the supply of oxygen can become quite critical. Whatever the oxygen supply is, it must produce at least three oxygens for every aluminum atom for the process to be properly carried out. It is noted that the oxygen is not used in an intermediate function. It is used to form the hydroxyl groups and also to form any active oxygen which is held in clathrate form. Thus, if all the hydroxyl groups are supplied from a source of the same, such as water, no oxygen will be needed. On the other hand, if part of the supply of hydroxyl groups comes from a source of the same and part is made up from oxygen and protons, then only sufficient oxygen to make up the latter amount of hydroxyl groups will be needed. This is the usual situation and will reduce the supply of oxygen needed. As previously mentioned, there is also a small amount of oxygen which may be trapped within the lattice structure of the product. However, it is not part of the structure, but sufficient oxygen should be nevertheless supplied for it to take place. This oxygen in clathrate form is referred to as active oxygen.

It has also been found that humidity plays an important part in the efficient development of the complex of the present invention. It appears that the higher the humidity is, the higher the static electricity is, and the better off the reaction proceeds. In other words, on a stormy day where the static electricity may be in the vicinity of 10,000 volts, the reaction will proceed at a rapid rate. The reason for this is that as the humidity increases, the pressure decreases and lower external pressure will cause the reaction to proceed at a more rapid rate. However, the humidity limits are not as critical as the temperature limits.

It has also been found that protons and OH− groups can be easily picked up from the moisture in the atmosphere. Thus, it is desirable from this aspect to keep the moisture in the atmosphere at around the 85% figure. If necessary, a humidifier may be installed to maintain the humidity in the atmosphere surrounding the process at this 85% figure. Also, higher static charge can cause a greater potential difference between the mercury and the aluminum to increase the field effect.

It is most probable that the following chemical and reactions occur. Basically, the aluminum which is preferably at least 99.9% and most preferably 99.98 or 99.99% purity must be relatively free of surface oxidation. These oxides may be removed by any of the halogen acids as aforementioned. Hydrochloric acid is a particularly suitable acid for doing this. Of course, the halogen acids do not have to be used since any normal conventional scraping or any oxide removal technique can be used to accomplish the same result. Hydrochloric acid strips the surface oxide from the aluminum by a relatively well-known process. While aluminum oxide is not soluble in hydrochloric acid, the vapor pressure of hydrochloric acid is sufficiently great to permeate the oxide and attack the metallic aluminum therebeneath. The hydrochloric acid, in attacking the aluminum, etches the aluminum sufficiently so as to break down the interface between the oxide and the aluminum of the surface oxidation. The removal of oxides is essential since it has been found that the complex of this invention will not be produced on the surface of the aluminum where oxides are present. The reason for this is that mercury will not permeate the aluminum where there is an oxide layer on the surface of the aluminum or a hydrogen ion source is absent. Once the aluminum has been stripped of oxide, the mercury then can effectively permeate the aluminum in the presence of hydrogen ions. In the usual process, the aluminum is already positioned in the mercury bath at this point so that once the aluminum is deoxidized, the process can proceed. However, the process can proceed in two separate steps. First, the aluminum can be deoxidized and then placed in the mercury. Instead of the aluminum being placed in a mercury bath, the mercury can be poured over the aluminum. An initial amount of heat is generated by the exothermic reaction between the halogen acid and the aluminum. This heat in combination with electron collisions causes the beginning of the generation of ultraviolet radiation. The ultraviolet radiation, though, is principally caused by collisions between electrons and particles with the mercury electrons. As the process continues, a substantial amount of heat is generated from within the aluminum itself. This appears to be due to the formation of the complex of this invention and indicates that the process is substantially exothermic and thus requires a heat sink (a method of cooling) to keep the process at the proper operating temperature. This heat sink as aforementioned is provided by the mercury. At the start of the process, the free protons (hydrogen ions), which are generated by the ionization of the halogen acid, begin to permeate through the aluminum during the reaction between the halogen acid and the aluminum. These protons act in concert with the mercury. The two together appear to act as a plasma and permeate through the lattice structure of the aluminum. If either one is absent, the other will not permeate through the aluminum. The permeation continues until the aluminum is completely saturated with mercury. It is believed that the mercury occupied the available spaces between the grain boundaries in the matrix and does not actually penetrate any of the grains, but simply penetrates the space therebetween. The mercury penetrates to the saturation point such that it weakens the entire bond structure of the aluminum to the point where the aluminum hardness as aforementioned is reduced to the hardness of babbit metal. It is, therefore, surmised that the mercury, in permeating the aluminum, interferes with the interatomic bonds between the aluminum atoms to weaken these bonds. At this point, the mercury source can be removed since no more mercury can enter into the process as the aluminum has been completely permeated (saturated) by mercury. The aluminum can be placed in the reagent (halogen acid) and the process will continue as before since no more mercury is needed. If desired, the aluminum can be left in the mercury without any adverse effects.

The heat of the exothermic reaction between the aluminum and the halogen acid raises the energy level of the outer orbit electrons of the mercury atoms to an energy level higher than their normal energy state. In this condition, the mercury atoms become unstable and cause collisions between aluminum electrons and fragmentary particles and other electrons. These collisions will generate ultraviolet radiation. This reaction, which takes place within the aluminum itself, can be represented by the following equation.

| Where | Hg | represents mercury in an unexcited state; |
|---|---|---|
| Where | DH | represents the input energy carried or transferred by the collisions of electrons and mercury electrons. |
| Where | Hg | represents mercury in an excited state; |
| Where | U | represents ultraviolet radiation. |

It is believed that resonance then occurs between the mercury reaction set forth above and a halogen ion such as a chloride ion and hydrogen gas in the following manner. The two will react with explosive violence under ultraviolet radiation to generate sufficient heat to cause collisions to generate more ultraviolet radiation. Thus, a resonance will be established between the collisions and the halogen and hydrogen reaction to cause the continual generation of ultraviolet radiation. The reaction that causes the halogen to absorb ultraviolet radiation to being this reaction is as follows:

| Where | Cl | represents chloride ion in an unexcited state; |
|---|---|---|
| Where | $\overset{+}{Cl}$ | represents a chloride in an excited state; and |
| Where | φ | represents photons |

In a similar manner, hydrogen gas is released by the exothermic reaction between the halogen acid and aluminum. It has been observed that the conversion of aluminum to the complex of this invention is greatly enhanced by passing hydrogen gas over the aluminum when it is in contact with the halogen acid. It is, therefore, believed that hydrogen atoms are also excited by the ultraviolet radiation from the collisions in the same manner as the halogen ion. Decay of the excited hydrogen atom further releases photons represented by the following equation:

| Where | $H_2$ | represents hydrogen in an unexcited state; and |
|---|---|---|
| Where | $\overset{+}{H_2}$ | represents hydrogen in an excited state. |

Photons generated by both the decay of the excited halogen ion and the excited hydrogen atom are absorbed by mercury atoms, raising their energy level to a higher energy state and thereby, their orbital electrons to a higher energy state. These mercury atoms then decay to their original state, thereby releasing additional energy as ultraviolet radiation, which continues until a resonance occurs between the mercury atoms, halogen ions and hydrogen atoms. When resonance finally occurs, there is a sufficient continual source of ultraviolet radiation in the aluminum to sustain the complete conversion of the aluminum to the complex. It is essential that the ultraviolet radiation or other radiation as aforementioned be generated to cause the reaction to take place.

The aluminum crystal is known to contain approximately 12 electrons at the juncture of the aluminum atoms. What is believed happens is that ultraviolet radiation of approximately 700–3,000 Angstroms (wavelengths) causes one or more of the aluminum atoms in the crystal either to rupture or distort, or possibly cause the outer electron band to raise its energy level as a result of this ultraviolet radiation, to the extent that the crystal lattice of the aluminum is distorted. As this distortion is taking place, the protons which are passing through the aluminum combine with the aluminum and with oxygen atoms, which as aforementioned, can be present in the atmosphere surrounding the process. Hydroxyl radicals can also be absorbed into the complex. These can be present in the aqueous solution of the halogen acid. The hydrogen and oxygen and aluminum then combine and the complex of this invention begins to form on the aluminum.

A key feature of the process is the establishment of an electromagnetic field about the aluminum. This field is established between the aluminum and mercury with the assistance of the hydrogen ion source. The field is referred to as the fountain effect. It passes through the aluminum to form a fountain-like oval path on each side of the aluminum. The field, being in constant motion through and outside the aluminum, transports hydrogen ions from the halogen acid or other source of hydrogen ions through the aluminum so that they are in a position at the top surface of the aluminum where they can combine with the aluminum and the oxygen (which is present at the top surface of the aluminum) and the hydroxyl groups. The theory behind the formation of this field is as follows: The aluminum and the mercury are of different electrical potentials. This difference in potentials creates an electromagnetic field effect that travels from the metal of lower potential (aluminum) to the metal of higher potential (mercury). The field which is an electromagnetic wave motion travels in a path from between the aluminum and the mercury through the halogen acid, through the mercury, through the aluminum and back between the aluminum and mercury. The difference in potential which produces the field actually produces an electrical charge differential between the two metals, (one metal being more positive than the other; mercury being more positive than aluminum) which causes a charge migration between the two to cause the field effect action.

The field effect is aided by the electrolytic action in the halogen acid; for example, HCl ionizes into the negative halogen ions and protons. The halogen ions are attracted towards a downward motion that is in the same direction as the electromagnetic field and therefore, adds strength to the field. This causes the hydrogen ions and the mercury to travel through the aluminum. Without the field, a few hydrogen ions and some mercury would enter the aluminum, but they would not travel into the aluminum far enough to cause the present reaction; but with the field they travel completely through the aluminum. The existence and the strength of the fountain effect are key features of the process.

Also, the field effect is significantly affected by atmospheric conditions. At reduced atmospheric pressure or partial vacuum, the fountain effect is dramatically increased because the pressure is substantially reduced. Reduced pressure causes less resistance to the flow of hydrogen ions through the aluminum. As a result, the complex of this invention is produced at an accelerated rate. In view of this, a much larger diameter electrode may be used since the field can travel much higher. It is also to be appreciated that not only the atmospheric pressure but also gravitational forces substantially affect the field since the gravitational forces retard the progress of the hydrogen ions through the aluminum. If these gravitational effects are reduced, such as on the moon for example, the complex would form many times faster because of this reduction in pressure. Also, after the aluminum is completely saturated with mercury, it can then be placed in a shallow bath of the proton source alone and will continue to form. No more mercury is needed since the aluminum is saturated with mercury. A good proton source for this purpose appears to be a halogen hydrate. These halogen hydrates provide all the functions of the source of hydrogen ions, especially that of providing a substantial amount of hydrogen ions.

It has also been found that the mechanical level of the source of protons, e.g., halogen acid, in and about the aluminum is also important when employing a mercury bath. The halogen acid must form an extremely thin film over the surface of the mercury. It has been found that if the halogen acid film is excessive, it tends to act as a heat sink, cooling the reaction and washing away the complex before it has time to form as an upwardly extending curtain. The thickness of the halogen acid film must be controlled to permit development of the complex curtain on the exposed surface of the aluminum. An ideal thickness of the film is in the order of 0.015 inches.

Reaction Technique

1. An aluminum rod having a diameter of five-eighths inch is bent into a circle lying in the same plane. The aluminum should have less than 0.01% impurities.
2. The aluminum rod is treated with a concentrated halogen acid such as hydrochloric acid, 2N, to strip surface oxides. Alternatively, the surface oxides can be stripped by any other standard chemical or mechanical means (such as abrading).
3. The rod is laid in a shallow, toroidal or linear glass or plastic dish having a flat bottom and filled with liquid mercury sufficient to expose the aluminum rod along its entire length above its midpoint.
4. 0.5 Normal concentrated halogen acid such as hydrochloric acid is floated on the surface of the mercury adjacent to the aluminum rod so to create a relatively thin film, i.e., on the order of 0.015 inch, of hydrochloric acid extending over the rod.
5. The reaction is permitted to proceed with the temperature of the aluminum rod immediately adjacent to its surface being maintained at approximately 100° F. A curtain of the compound forms on the top exposed surface of the aluminum rod and extends upwardly.
6. The electromagnetic field effect and the temperature of the reaction may be controlled by controlling the depth of immersion of the aluminum rod in the mercury.
7. Alternate means of controlling the temperature reaction may be provided in the form of a heat exchanger beneath the reaction vessel.
8. The relative humidity of the ambient atmosphere should be approximately 50–96% and humidification can be provided to keep it at this humidity, and the air in and about the surface of the aluminum rod must be relatively still.
9. The compound forming as an annular curtain on top of the aluminum may be removed periodically as desired, e.g., by simple mechanical means such as scraping, blowing, etc.
10. Once the reaction has started, the aluminum rod can be removed from the mercury bath and placed in a bath of the halogen acid or hydrate and the reaction will proceed as before. This is because once the reaction has started the aluminum has been completely saturated with mercury and no more mercury is needed. It is noted that the aluminum rod is eroded from above and not from below. This is due to the complex taking aluminum atoms from the top of the rod to form. Because there is a wearing away of the rod only on top, the rod is turned over every so often to provide symmetrical wearing. If the aluminum rod is positioned improperly, too low or too high in the mercury during reaction, the erosion may result in a cross sectional configuration which is vertically elliptical or triangular. This is due to the electromagnetic field being produced at the sides of the rod as aforementioned.

A careful observation of the complex forming on the exposed surface of the aluminum above the level of the mercury bath discloses that the complex appears to be in contact with the surface of the mercury which coats the aluminum and not in actual contact with the aluminum. The compound appears as an extremely lightweight, delicately bluish-white, still structure which may be broken up into chunks.

While the above technique is preferably for many reasons, many other techniques may be employed which will produce the complex of the present invention.

Figure 1:
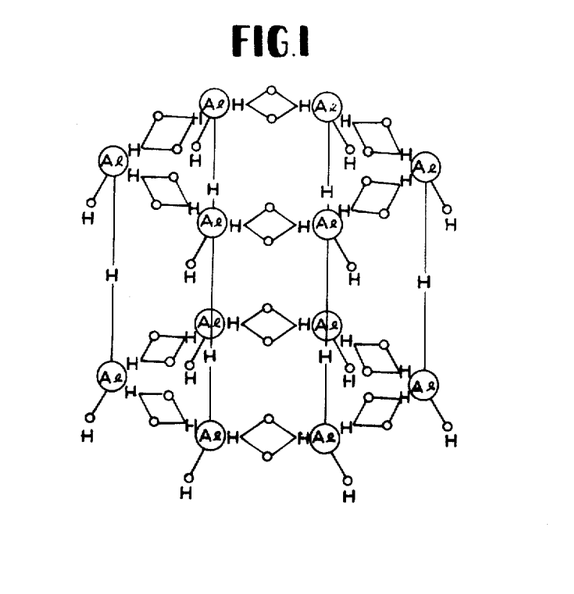
FIG. 1 illustrates the proposed molecular structure of the complex of the present invention.
Figure 2:
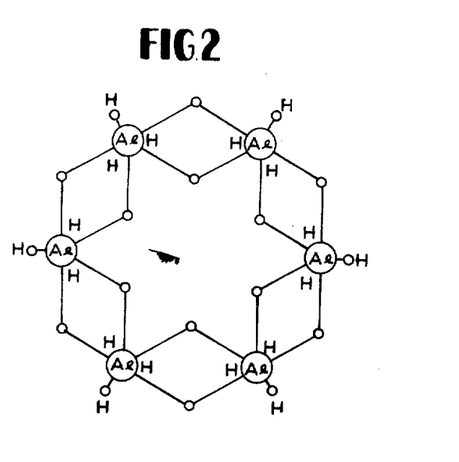
FIG. 2 illustrates one platal of the proposed structure of FIG. 1.

The structure of the complex described herein can be postulated; however, it will be appreciated that the structure of the complex is not postulated with any absolute degree of certainty. As shown in FIG. 1 and 2, the proposed structure which has been verified to some degree by the procedures mentioned subsequently consists of a hexagonal structure consisting of two platals which are connected by two hydrogen atoms and two oxygen atoms (probably arranged in a peroxy group). These peroxy groups appear to be in the same plane as the platals.

The actual connection between the peroxy groups and the aluminum atoms is as follows: As shown in FIGS. 1 and 2, each aluminum atom has to hydrogen atoms connected to it in close proximity. Each of these hydrogen atoms are connected by two oxygen bridges to a hydrogen atom on the next adjacent aluminum atom. There are then two oxygen atoms and two hydrogen atoms which connect every two aluminum atoms. This same structural configuration exists between all six aluminum atoms so that they are held together in a ring configuration. There is a hydroxyl group extending from each Al atom at a slight angle to vertical (almost perpendicular to the plane of the platals). This hydroxyl group is especially reactive since it has a free end. The other platal which is identical is positioned below this platal and is connected to it by hydrogen bridges (hydrogen ions which are connected approximately between the aluminum in the top platal and the bottom platal). The entire structure is between 7–15 Angstroms in width from one aluminum to the diagonally opposite located aluminum atom in the same platal.

Figure 3:
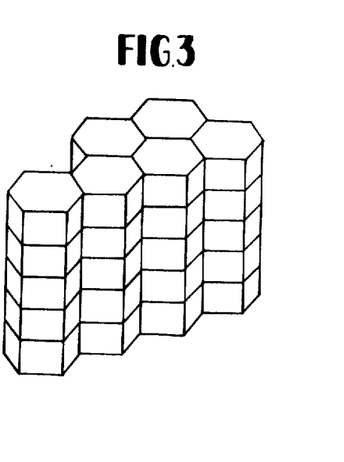
FIG. 3 illustrates a proposed arrangement of a group of molecules of FIG. 1.

The chemical formula for the substance can then be postulated as $Al_{12}(H_2O_2)_{18}H_6$. FIG. 3 shows a group of these molecules arranged in a close-packed array and interconnected by the aluminum atoms and the hydroxyl groups.

The individual molecules form into long, polymeric chains of molecules, 40–200 Angstroms in length. The structure of the molecules in these chains is, of course, exactly the same and they are physically connected together by the hydrogen bridges (each platal is connected to the next platal by these bridges). The bridges prevent the platals from flying apart. Each of the platals would appear to have an overall negative charge; however, when they are formed into the ring structure and when the positively charged protons (the hydrogen bridges) are linked to them, the entire structure is stabilized into a long chain polymer. These polymers then group together to form the clusters as shown in FIG. 3, which have a width of about 40 Angstroms. These clusters as aforementioned are held together by the aluminum atoms and the free hydroxyl groups. These hydroxyl groups position themselves between the oxygens of the peroxide groups of the adjoining molecules. While each of the rings itself may be highly unstable, the entire polymer, because of the interconnection and the hydrogen bridges, is quite stable. There also appears to be a small amount of oxygen which is held in clathrate form within the structure of the compound. Since it is in clathrate form, it is not structurally bound to the compound but nevertheless, exists therein. This oxygen is probably in the form of $O_3$ with some $O_2$ present.

Figure 4:
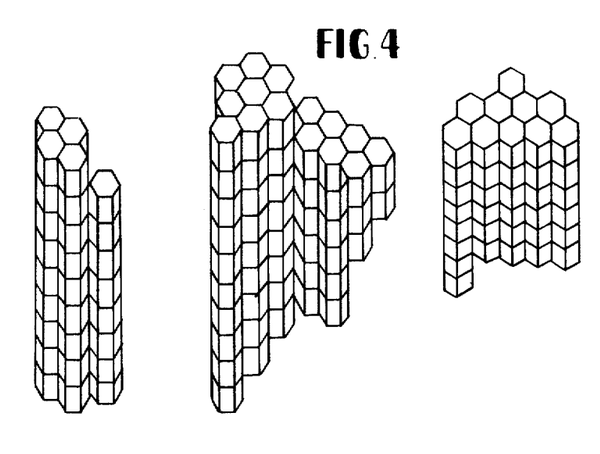
FIG. 4 illustrates an aligned variety of FIG. 3.
Figure 5:
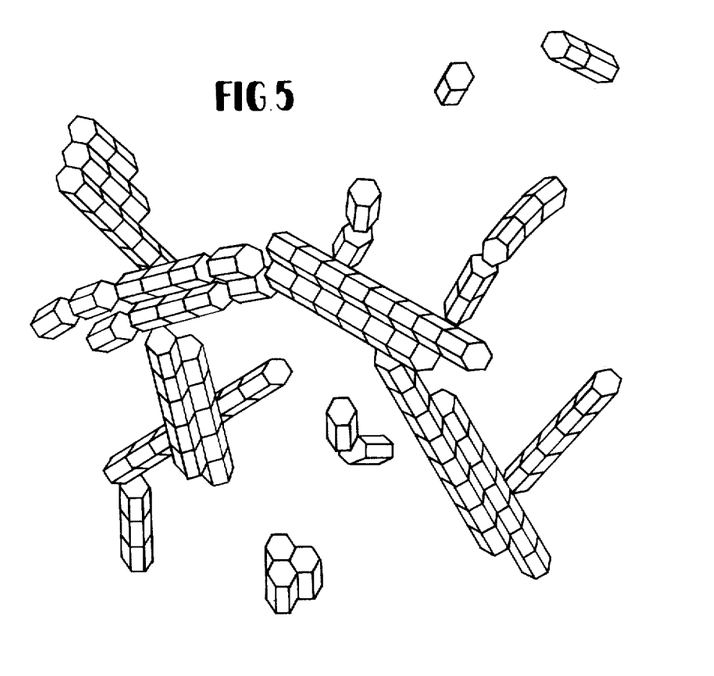
FIG. 5 illustrates a non-aligned variety of FIG. 3.

There are basically two distinct structural varieties, the aligned (FIG. 4) and the non-aligned varieties (FIG. 5) (the dense and loose varieties). The molecules of the two are exactly the same. The difference is that chains are not as long or as linear in the non-aligned variety (loose variety). This appears to be caused by the nonexistence of some hydrogen bridges. Platals are attached to other platals without any hydrogen bridges being present, and thus, fewer monomers are attached together. There is also less clustering in this variety as is shown in FIG. 5.

As analysis of the two structures shows that less hydrogen and less proton bridges are present in the non-aligned variety and its formation is therefore less exothermic (less protons passing through the aluminum) than the aligned variety; less hydrogen as aforementioned would indicate fewer hydrogen bridges and shorter chains.

The major difference in producing the two structures is that since the non-aligned variety contains less hydrogen operation at lower temperatures, room temperature or lower, will cause this result.

FIG. 6 is a pH curve of the complex plotting increasing pH vs. increasing time of a 0.5% aqueous suspension of the complex of this invention. The purpose of this curve is to show the parts of the complex as it breaks up. At first, the complex is at neutral pH, or 7. Almost immediately (two hours), the hydrogen bridges between the platals begin to dissolve in the aqueous solution and the pH becomes increasingly acidic, going almost in a straight vertical line from 7 to approximately 4.5. This proves the existence of a significant amount of hydrogen ions in the complex and also indicates that it is held in a manner so that it is first to break off. The bridges are in this vulnerable position. Then, more slowly, the complex begins to break up and the peroxide groups then go into solution. As they go into solution, the solution becomes increasingly less acidic and more alkaline until it goes back to neutral condition and even to pH8 because of excess $OH^-$ ions. This proves the existence of the large amount of oxygens and hydrogens. A more complete analysis of this is as follows:

In the first 2 hours in the aqueous solution, the water will slowly penetrate the fibril structure. This will cause some hydrogen bridges to be leached away from the structure, which will cause the balance of the structure to be upset and the structure to collapse. Following the collapse, more hydrogen bridges will be liberated.

The pH at this time will drop drastically from 7 to 4.5 because of the sudden increase of $H^+$ ions in solution. Following this, the peroxide groups will start to break up. This will result in the collapse and liberation of the hydrogens, the oxygens and the oxygen ions, including some entrapped oxygen ($O_3$) held in clathrate form. At this point, there will be a regrouping of the hydrogen ions and the oxygen ions (the $OH^-$) into water by nucleation, and the pH will rise. During the first ten hours there will be an increase and a decrease in the pH level, the pH rising to 5.5 and falling back to 5 due to the further breaking up of the structure. After about twenty hours, the cells will become completely separated and the entire structure will break down. At this point, the pH will rise to above its original level (about 8). This rise can be accounted for by the large amount of OH⁻ group from the peroxides breaking up and going into solution, and thereby substantially raising the alkalinity. This pH analysis proves the existence of the H bridges and the large amount of OH⁻ groups.

Another analysis of the structure can be seen in FIG. 7, which is an infra-red graph of the structure. In this graph it will be seen that between approximately 3750 and 2600 there is a huge bend in the curve. This can be accounted for by the infra-red scanning incurring a very wide band of oxygens and hydrogens (the peroxys). It is customary to expect infra-red to encounter these in this wavelength range. This is proof of the large amount of peroxys which occur in the complex. The next significant points in the infra-red curve occur at approximately 1700, 1500 and 1400. At these points there are three dips. These are at the wavelengths where one would expect to incur hydrogen. This would tend to confirm the existence of the three hydrogen bridges. The infra-red rays will only be able to "see" three of the six bridges. The other three are behind the first three and thus will not be incurred by the infra-red. The final dip in the curve at about 850 can be accounted for by free oxygen, the small amount of oxygen that is entrapped in the structure. This is considered held in a clathrate form. As aforementioned, this oxygen is not part of the complex structure. To produce this infra-red graph, a sample was placed in a desiccator for 239 hours until constant weight had been reached. After 7.1% weight loss, a potassium bromide pellet structure was obtained. Some other points of interest in the curve are: The wide absorption at 3400 chain molecular structure due to the large OH concentration. Also, the Al-O stretch and the Al-HO bend would prove the structure, which is part of the basic structure of the complex.

An X-ray analysis of the structure was also run. An untreated sample was calcined at various temperatures. The X-ray analysis and the infra-red analysis were generally in accordance with each other, in that both methods indicated an identical chemical composition. X-ray defraction analysis of dried samples showed the material to be amorphous. These X-rays will indicate an amorphous structure even if it is crystalline if the structure is smaller than 40 Angstroms. From other data, it is proven to be crystalline and it is substantially below 40 Angstroms in size. It appears to be between 7–15 Angstroms.

A differential thermal analysis was also run. This also supported the X-ray defraction and infra-red analysis. The differential thermal analysis curve was condensed and is shown in FIG. 8. This indicates an endotherm at approximately 100° C. where the absorbed water is released. An exotherm between 600° C. and 1000° C. and 1250° C. caused by the final re-crystalization to alpha alumina and finally, a sharp endotherm exists at approximately 1300° C. as a result of grain growth of the fine alpha alumina particles. This is substantially different from the normal curve for $Al_2O_3$.

Am emission spectrographic analysis was also run. This confirmed the other results and showed only those elements which were expected and no significant trace elements were found. This should bear out the fact that the complex contains essentially only aluminum, oxygen and hydrogen as previously mentioned.

A determination of the specific gravity of the complex was made. This was done with a pycnometer at 20° C. in n-octane as the suspending medium (spectro grade). A 50 ml. specific gravity flask (conical shape) with a ground joint for the thermometer (range 14° C. to 37° C., 0.2° C. intervals) was used in accordance with ASTM specifications. Two 1.500 gram samples were chosen; one was new, and the other was fairly old. The samples were agitated with a magnetic stirer to insure the breaking up of larger particles and the total wetting of the samples by the n-octane. Three measurements were made with each sample, and were as follows:

| Specific Gravity | Old | Fresh |
|---|---|---|
| First determination | 0.9150 | 0.9230 |
| Second determination | 0.9220 | 0.9080 |
| Third determination | 0.9191 | 0.9119 |

The results appear to indicate a specific gravity of approximately 0.91 and also indicate that the specific gravity of the complex does not change with time.

EDTA tests have also been run to determine the peroxide number of the complex. This has been determined to be 2.9%. EDTA tests have also been run to determine the surface area of the complex. This has been determined to be 290–500 M²/gram at 250° C. However, at this high temperature some of the oxygens and hydrogens have been driven off and therefore, the surface area is less than it would be at room temperature. Tests have also been run to determine the magnetic resonance and surface charge. These are as follows: NMR spectra could not be obtained on the complex due to the magnetic moments of the structure including that of a quadrapole moment of $Al_{27}$ and polymeric nature of the aluminum in the structure did not allow measurement of the denicol shift. Further, tests show that the compound possesses a 2.2 ev surface charge and has bonding energies of less than 20 ev for the structure as a whole. The bonding charges are 8, 12 and 17 ev respectively from the outer atoms to the inner ones of the structure. Tests were also conducted to determine the approximate gel points for $M_gO$ suspension of the compound. Fresh samples and old samples of the compound were used for the tests. The results in length of time to gel were as follows:

| Concentration | 1% Mg. Fresh | No. Mg. 4 Year Old |
|---|---|---|
| 4.0% | 10 days | 12 days |
| 2.0% | 12 days | 16 days |
| 1.5% | 14 days | 20 days |
| 0.5% | ½ gelled after 4 mos. | ½ gelled after 4 months |
| 0.25% | still liquid after 4 mos. | still liquid after 4 months |
| 0.10% | still liquid after 4 mos. | still liquid after 4 months |

The gellation capacity appears to decrease slightly with storage and/or in the absence of Mg in the product and is also significantly different than any similar compounds. Other tests also indicated that the external hydroxyl group will break loose at 105°–120° C. and the remaining hydroxyl groups will break loose at 800° C.

Figure 9:
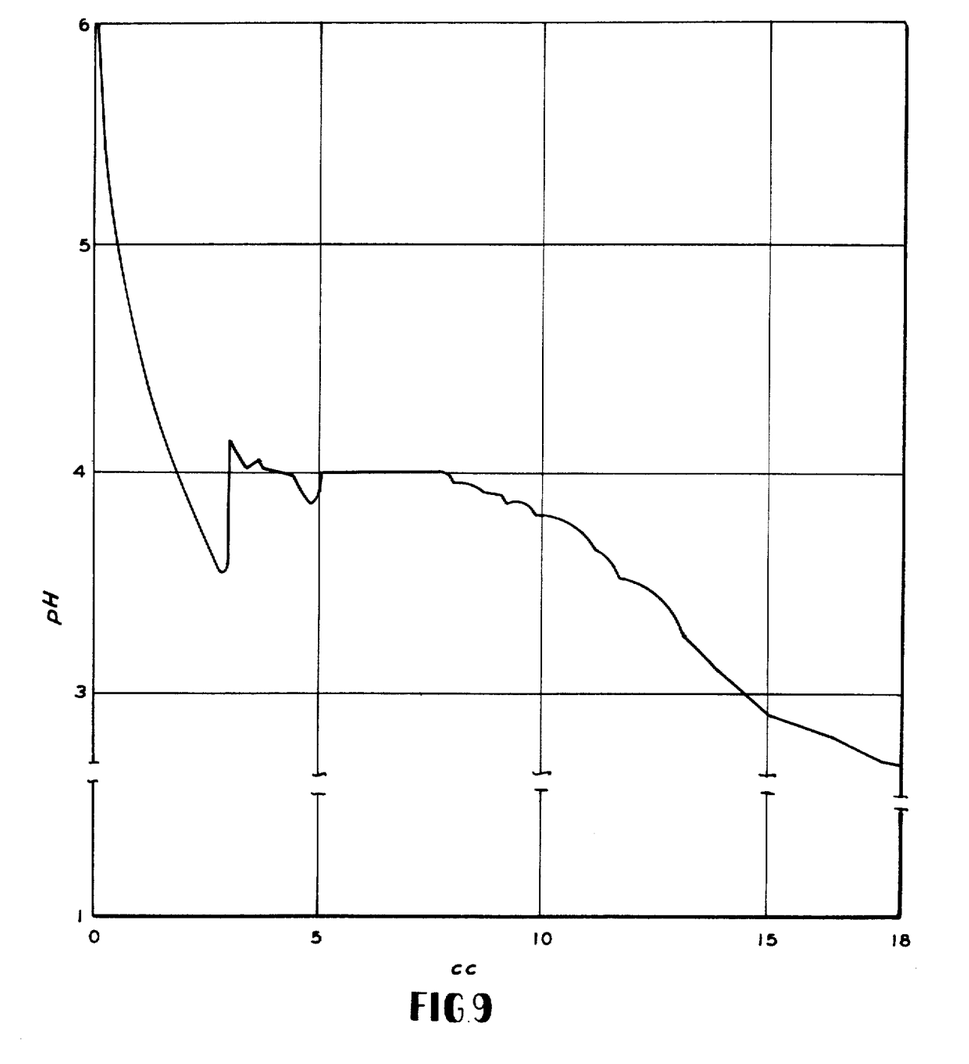
FIG. 9 is a titration curve of the complex of the present invention.

Titration was run with n/100 HCl as shown in FIG. 9. The results indicated a ratio of hydroxyl group to aluminum of 3.4 and also showed that the complex dissolves completely at a pH of 3.8. This is entirely different from known aluminum compounds, includng aluminum hydroxide.

FIG. 10 is an electron spin resonance curve of the complex. The curve showed a significant amount of hyperfine structures and the absence of 500 Gauss proton spectrum. This indicates that there is no appreciable unpaired spin density located in a hydroxyl group and tends to prove that no OH radicals as such exist, and thus, the bonds are probably peroxy bonds. The aluminums are bonded together not by hydroxyl groups, but by peroxy bonds ($HO_2$). A rather intense signal was obtained from the sample. The main signal was a g-value of 2.4, indicating a significant interaction between the unpaired electron spin with its orbital angular characteristic of metals, notably transition metals. This test confirmed the structure of the compound. It indicated a structure of H-Al H OO, which can be written as which is seen as part of the basic structure of the complex.

The method of the present invention will now be illustrated by reference to the following non-limiting examples.

EXAMPLE 1

(a) 100 grams of aluminum rod, having no more than approximately 0.0010% impurities by weight is bent into a circular form and placed in the bottom of a shallow, glass vessel;

(b) Liquid mercury is introduced into the vessel, covering approximately one-half of the cross section of the aluminum rod;

(c) 1.0 Normal hydrochloric acid is added to the vessel sufficient to float on the mercury and contact the aluminum rod at all points to provide a HCl film of about 0.015 inch.

(d) The mercury wetted aluminum rod is allowed to sit in the bath of mercury and in contact with hydrochloric acid film while the aluminum compound forms from the top of the rod upwardly;

(e) The temperature is approximately that of room temperature and the pressure is approximately atmospheric.

EXAMPLE 2

(a) 100 grams of aluminum rod having approximately no more than 0.0010% impurities by weight is placed in a glass vessel, the aluminum rod, lying flat therein.

(b) Approximately 18 ounces of approximately 1.0 Normal hydrochloric acid are gradually added to the vessel and the vessel vigorously agitated until the aluminum has been stripped substantially of surface oxides;

(c) Approximately 10 grams of powdered mercuric oxide, either red or yellow, are added to the vessel and left to convert to mercury, the rod will then rest at about its midpoint in the mercury.

(d) The vessel is permitted to stand open to the air until substantially all of the aluminum is converted to the complex of the invention.

(e) The temperature is maintained at approximately 70° F. during the reaction with the pressure maintained at ambient atmosphere.

EXAMPLE 3

(a) The procedure set forth in Example 2 is followed with the exception that mercuric chloride is substituted for mercuric oxide in the amount of approximately 40 grams.

EXAMPLE 4

(a) The procedure set forth in Example 3 is followed with the exception that mercuric sulfate is substituted for mercuric oxide in the amount of approximately 75 grams.

EXAMPLE 5

The procedure set forth in Example 2 is followed with the exception that the aluminum rod has been coated with mercuric oxide, and the mercuric oxide reduced to mercury. The temperature is reduced to approximately 75° F. whereupon the reaction proceeds at a greatly accelerated rate.

EXAMPLE 6

The procedure in accordance with Example 2 is followed with the exception that after the addition of mercuric oxide, the aluminum rod is irradiated with ultraviolet radiation in the wavelength range of approximately 1000 Angstroms from a suitable external source.

EXAMPLE 7

The procedure in accordance with Example 2 is followed with the exception that hydrogen gas is passed over the aluminum rod during and after the addition of mercuric oxide. The presence of hydrogen gas accelerates the reaction.

EXAMPLE 8

(a) 100 grams of aluminum rod having no more than approximately 0.010% impurities by weight and stripped of surface oxides is laid in a horizontal trough in a reaction vessel;

(b) The trough is partially filled with liquid mercury, such that a portion of the aluminum projects above the surface of the mercury and a quantity of 1.0 normal hydrochloric acid is added to the vessel sufficient to contact at least a portion of the aluminum rod extending above the mercury, leaving a portion of the aluminum rod in contact with the ambient atmosphere containing oxygen;

(c) The reaction is permitted to continue with an effective reaction temperature no greater than approximately 120° F. and, preferably, substantially lower until the final product aluminum material emerges as a lightweight solid growing on the surface of the aluminum rod, growing upwardly into the surrounding air.

EXAMPLE 9

(a) 1,000 grams, five-eighths inch diameter aluminum rod of 99.9% purity is placed into a reactor bed containing 1 quart of liquid mercury. The aluminum rod is floated in the mercury. Sufficient hydrochloric acid (;0.5N) is added to cover the rod completely. The reaction is allowed to proceed until the rod is completely saturated with Hg which takes about two hours. The excess HCl is now drained off so that a film of approximately 0.005–0.010 inch in thickness is maintained. This level is maintained throughout the reaction by automatic feed. The automatic feed filled to about 4,000 ml. This should be sufficient for the reaction to proceed to the extent of consuming one-half of the rod. After 24 hours the rod is turned around. One automatic feed is refilled and the reaction run until the rod becomes about one-sixteenth inch thick. The complex obtained constitutes approximately 20% of the total weight of the rod. The rod must lie in a plane in the reaction vessel free of any bend or deformation.

EXAMPLE 10

Example 9 is repeated except that when the aluminum rod has been saturated with mercury, the HCl, is drained as described. The mercury left in the reactor is replaced with aqueous aluminum chlorohydrate.

EXAMPLES 11 and 12

Examples 9 and 10 are repeated except that the HCl is replaced with HBr and aluminum bromohydrate, respectively.

EXAMPLES 13 and 14

Examples 9 and 10 are repeated except that the HCl is replaced with HI and aluminum iodohydrate, respectively.

EXAMPLES 15 and 16

Examples 9 and 10 are repeated except that the HCl is replaced with HF and aluminum fluorohydrate, respectively.

EXAMPLES 17-32

Examples 9-16 are repeated except that an organic acid such as acetic acid or an alcohol such as methanol is used instead of the halogen acids.

EXAMPLES 33-56

Examples 9-32 are repeated except that the 99.99% pure aluminum is replaced with aluminum containing 1% or more magnesium. The product obtained in each case is unstable and degrades to aluminum dihydrate or monohydrate.

EXAMPLES 57-66

Example 9 is repeated. Replace 99.99% pure Al by weight with 99.98% pure Al by weight containing no more than 0.05% by weight of one of the following: cesium, vanadium, zirconium, barium, lanthanum, hafnum, titanium, thallium palladium or niobium.

In the above examples a complex in the form of particles having an average particle size (diameter) within the range of 7-15 Angstroms is obtained. Polymer fragments having an average chain length within the range of 40-200 Angstroms and a width of up to 40 Angstroms are also recovered from the reaction product.

While the present invention has been described primarily with respect to the foregoing specific exemplification and illustration of preferred embodiments, it should be understood that the present invention cannot be deemed limited thereto, but, rather, must be construed as broadly as all or an equivalent thereof.

I claim:

1. A method of preparing a complex of aluminum, oxygen and hydrogen, which comprises reacting by contacting, at a temperature below 150° F., aluminum metal of a purity of at least 99.98% by weight with an aqueous inorganic halogen acid in the presence of mercury and an oxygen gas containing atmosphere, said aluminum being partially immersed in said mercury and said aqueous inorganic halogen acid comprising a thin film over said mercury, the thickness of said film being insufficient to cover the aluminum not immersed in said mercury, whereby a portion of said aluminum is exposed to said oxygen gas containing atmosphere, said complex growing from the surface of said aluminum exposed to said oxygen gas containing atmosphere in the form of an easily frangible self-supporting sheet; and collecting said complex.

2. The method of claim 1 wherein said aqueous inorganic halogen acid is aqueous hydrochloric acid.

3. The method of claim 1 wherein said aqueous inorganic halogen acid has a concentration of 0.1 to 2 normal.

4. The method of claim 1 wherein said thin film of inorganic halogen acid is about 0.015 inch in thickness.

5. The method of claim 1 further including passing hydrogen gas over said aluminum.

6. A method of preparing a complex of aluminum, oxygen and hydrogen which comprises reacting by contacting, at a temperature below 150° F. aluminum metal of a purity of at least 99.98% by weight permeated with from 1% to 2% by weight mercury, with an oxygen gas containing atmosphere, said aluminum being partially immersed in a thin film of an aqueous inorganic halogen acid or aqueous aluminum halohydrate, whereby a portion of said aluminum is exposed to said oxygen gas containing atmosphere, said complex growing from the surface of said aluminum exposed to said oxygen gas containing atmosphere in the form of an easily frangible self-supporting sheet; and collecting said complex.

7. The method of claim 6 wherein said aqueous inorganic halogen acid is aqueous hydrochloric acid.

8. The method of claim 6 wherein said aqueous inorganic halogen acid has a concentration of 0.1 to 2 normal.

9. The method of claim 6 wherein said thin film of inorganic halogen acid is about 0.015 inch in thickness.

10. The method of claim 6 further including passing hydrogen gas over said aluminum.

11. A method of preparing a complex of aluminum, oxygen and hydrogen which comprises: stripping aluminum metal of a purity of at least 99.98% by weight permeated with from 1% to 2% by weight mercury of surface oxide film, reacting by contacting at a temperature below 150° F the surface stripped aluminum metal with an oxygen gas containing atmosphere, said aluminum being partially immersed in a thin film of a source of protons, whereby a portion of said aluminum is exposed to said oxygen gas containing atmosphere, said complex growing from the surface of said aluminum exposed to said oxygen gas containing atmosphere in the form of an easily frangible self-supporting sheet; and collecting said complex.

12. A method of preparing a complex of aluminum, oxygen and hydrogen, which comprises stripping aluminum metal of a purity of at least 99.98% by weight of surface oxide film, reacting by contacting at a temperature below 150° F the surface stripped aluminum metal with a source of protons in the presence of mercury and an oxygen gas containing atmosphere, said aluminum being partially immersed in said mercury and said source of protons comprising a thin film over said mercury, the thickness of said film being insufficient to cover the aluminum not immersed in said mercury, whereby a portion of said aluminum is exposed to said oxygen gas containing atmosphere, said complex growing from the surface of said aluminum exposed to said oxygen gas containing atmosphere in the form of an easily frangible self-supporting sheet; and collecting said complex.

* * * * *